United States Patent [19]

Handelsman et al.

[11] Patent Number: 4,878,936

[45] Date of Patent: Nov. 7, 1989

[54] METHOD TO ENHANCE ROOT NODULATION IN LEGUMES AND INOCULUM PREPARATION THEREFOR

[75] Inventors: Jo E. Handelsman; Larry J. Halverson, both of Madison, Wis.

[73] Assignee: Wisconsin Alumni Research Foundation, Madison, Wis.

[21] Appl. No.: 77,937

[22] Filed: Jul. 27, 1987

[51] Int. Cl.[4] .................... C05F 11/08; C12R 1/085
[52] U.S. Cl. ........................................ 71/7; 47/57.6; 47/58; 435/834
[58] Field of Search .................. 71/7; 47/57.6, 58; 435/834

[56] References Cited

U.S. PATENT DOCUMENTS

| | | | |
|---|---|---|---|
| 4,155,737 | 5/1979 | Dommergues et al. | 71/7 |
| 4,161,397 | 7/1979 | Bellet et al. | 71/7 |
| 4,259,317 | 3/1981 | Vesely | 424/93 |
| 4,367,609 | 1/1983 | Lloyd | 47/57.6 |
| 4,517,008 | 5/1985 | Strobel et al. | 71/77 |

OTHER PUBLICATIONS

Buchanan, R. E., *Bergey's Manual of Determinative Bacteriology*, 8th Ed., pp. 532–535 (1984).
Wakayama et al., "Mycocerein, a Novel Antifungal Peptide Antibiotic Produced by *Bacillus cereus*," *Antimicrobial Agents and Chemotherapy*, 26:6, pp. 939–940 (1984).
N.S.S. Rao, ed. *Current Developments in Biological Nitrogen Fixation* (1984), pp. 37–65.
Kamicker & Brill, "Identification of *Bradyrhizobium japonicum* Nodule Isolates from Wisconsin Soybean Fields," *App. & Env. Micro*, 51:3, pp. 487–492 (1986).
Gurusiddaiah et al., "Characterization of an Antibiotic Produced by a Strain of *Pseudomonas fluorescens* Inhibiting to *Gaeumannomyces graminis* var. *tritici* and *Pythium* Spp." *Antimicrobial Agents and Chemotherapy*, 29:3, pp. 488–495 (1986).
Misaghi et al., "Fungistatic Activity of Water–Soluble Fluorescent Pigments of Fluorescent *Pseudomonads*," *Phytopathology*, 72:1, pp. 33–35 (1982).
Howell and Stipanovic, "Suppression of *Pythium ultimum*-Induced Damping-Off of Cotton Seedings by *Pseudomonas fluorescens* and Its Antiobiotic, Pyoluteorin," *Phytopathology*, 70:8, pp. 712–715 (1980).
Howell and Stipanovic, "Control of *Rhizoctonia solani* on Cotton Seedings with *Pseudomonas fluorescens* and with an Antibiotic Produced by the Bacterium," *Phytopathology*, 69:5, 480–482 (1979).
Plazinski and Rolfe, "Influence of *Azospirillum* Strains on the Nodulation of Clovers by *Rhizobium* Strains," *Appl. and Env. Micro.*, 49:4, pp. 984–989 (1985).
Yahalom et al., "*Azospirillum* Effects on Susceptibility to *Rhizobium* Nodulation and on Nitrogen Fixation of Several Forage Legumes," *Can. J. Microbiol.*, 33, pp. 510–514 (1987).
Handelsman, "Abstract" on the isolation of *Bacillus cereus* presented at a meeting on or after Jul. 26, 1986.
Handelsman, et al., "Zoospore Lysis in Biocontrol of *Phytophithora Megasperma* by *Bacillus cereus* VW 85," Abstract presented Aug. 1987.

*Primary Examiner*—William R. Dixon, Jr.
*Assistant Examiner*—Andrew Griffis
*Attorney, Agent, or Firm*—Quarles & Brady

[57] ABSTRACT

A method for enhancing nodulation in legumes growing in a growing medium. The method includes the step of placing in the growing medium in the immediate vicinity of the roots of the legume the nodulation of which is to be enhanced an effective quantity of an enhancing bacteria selected from the group consisting of ATCC 53522, enhancing mutants of ATCC 53522, a mixture of such mutants, and a mixture of such mutants with ATCC 53522.

4 Claims, No Drawings

METHOD TO ENHANCE ROOT NODULATION IN LEGUMES AND INOCULUM PREPARATION THEREFOR

TECHNICAL FIELD

The present invention relates to enhancing the formation and development of root nodules in legumes, and, in particular, to doing so by means of a bacterial inoculant.

BACKGROUND OF ART

The formation and development of root nodules in legumes is important to the robustness of the plant and to the enhancement of available nitrogen concentrations in the soil. Conventionally, root nodulation has been encouraged by inoculating fields with bacteria appropriate for uptake into nodules. Even the Romans transferred soil from successful legume fields to unsuccessful legume fields with the knowledge that such a practice eventually could improve the quality of the poor fields. The same thing was done in the American Midwest when alfalfa first was introduced from Europe. European soil was brought along as an inoculant.

The soil bacteria found to be important to nodulation are members of the Rhizobium genus. Not all Rhizobium strains nodulate equally well, however, and some strains induce nodules effectively but do not fix nitrogen. When fields are thoroughly populated with such a strain of Rhizobium, inoculating the field with a new, superior Rhizobium species that forms robust nodules and efficiently fixes nitrogen may not be a successful way of enhancing the nitrogen-fixing performance of the legumes planted in the field. Because of the competition of Rhizobium already in the field or for other reasons not known, such Rhizobium inoculants tend not to be taken up by the plant, even when applied as seed coatings or when the ground immediately in the vicinity of a seed is separately inoculated with the improved Rhizobium. See: Kamicker, B. S. and J. J. Brill (1986), "Identification of *Bradyrhizobium japonicum* Nodule Isolates from Wisconsin Soybean Farms," *Appl. Environ. Microbiol.*, 51, 487–492.

BRIEF SUMMARY OF THE INVENTION

The invention is summarized in that a method for enhancing nodulation of legumes growing in a growing medium includes the steps of placing in the growing medium in the immediate vicinity of the roots of the legume the nodulation of which is to be enhanced an effective quantity of an enhancing bacteria selected from the group consisting of ATCC 53522, enhancing mutants of ATCC 53522, a mixture of such mutants, and a mixture of such mutants with ATCC 53522.

The inoculum of the invention for application to seeds for the enhancement of root nodulation in plants growing therefrom includes a non-interfering carrier and an enhancing bacteria selected from the group consisting of ATCC 53522, enhancing mutants of ATCC 53522, a mixture of such mutants, and a mixture of such mutants with ATCC 53522.

DETAILED DESCRIPTION OF THE PREFERRED EMBODIMENT

A bacterial strain has been isolated from soil that is effective in encouraging and enhancing nodulation in legumes. The strain has been deposited in the American Type Culture Collection, given the designation ATCC 53522, and shall hereinafter be referred to as "ATCC 53522." It has further been discovered that certain mutants of ATCC 53522 also are effective in enhancing nodulation in legumes in a manner comparable to the effect of ATCC 53522. These bacteria have been obtained in substantially pure cultures. A "substantially pure" culture shall be deemed a culture of a bacterium containing no other bacterial species in quantities sufficient to interfere with replication of the culture.

The method by which such nodulation enhancement may be verified to exist with respect to a particular mutant of ATCC 53522 will be referred to as the "nodulation enhancement test." Nodulation is "enhanced" if, when an effective quantity of ATCC 53522 or its mutants that exhibit enhancement of nodulation is placed in the soil or other growing medium in the immediate vicinity of the seed for or roots of plants in which nodulation is to be enhanced, a statistically significant increase in the weight, numbers, size, o longevity of nodules formed on the roots occurs. An "effective quantity" to enhance nodulation shall be that quantity sufficient to result in such a statistically significant enhancement of nodulation by the least significant difference test. Clearly, if no quantity of a bacterium is an effective quantity as so defined, that bacterium is not capable of exerting enhancement of nodulation. Bacteria or other materials shall be deemed placed in the "immediate vicinity" of a seed or roots if any soluble material so placed, any soluble exudate of the bacteria, or bacterial cells will be in actual contact with the seed as it germinates or the roots as they grow and develop. ATCC 53522 and those of its mutants capable of enhancing nodulation in legumes shall sometimes be referred to collectively or individually as "enhancing" bacteria.

ATCC 53522 was one of some 500 bacterial strains isolated from alfalfa roots and accompanying soil obtained from fields at the University of Wisconsin Experimental Farms at Arlington, Wis. and Marshfield, Wis., and from two private farms at Verona, Wis., and Cross Plains, Wis. The roots were cut into 1 cm. segments and each segment was placed in 10 ml. of sterile, distilled water. The root segment and water then were sonicated at twenty percent (20%) maximum power with a Vibra-Cell 250 watt sonicator obtained from Sonics and Materials, Inc., Danbury, Conn. Sonication was continued for 15 seconds. The sonicated mixture then was diluted in sterile, distilled water, and the dilutions were placed on trypticase soy agar (hereinafter referred to as "TSA") in petri plates to form dilution plates. TSA contains 30 g/l trypticase soy broth (hereinafter referred to as "TSB") obtained from BBL Microbiology Systems, Inc., Cockeysville, Md., and 15 g/l agar. TSA and TSB are conventional bacterial culture media well known to those skilled in the art.

The dilution plates were incubated at 28° C. for two days. For each root sample, bacterial colonies were selected from the dilution plate that had the highest number of distinguishable colonies. One colony of each visually distinguishable morphology on the plate was sampled with a sterile loop and was plated on a new TSA culture plate to allow the development of colonies in plates free from contamination by other bacteria. After two days incubation at 28° C., a single colony was selected from the resulting bacterial growth and was used to inoculate a TSA slant. The resulting slant cultures were stored at 4° C. until they were screened by an assay designed to detect bacteria capable of protecting plants from the root rot and damping off that are caused by members of the *Phytophthora genera.*

In particular, each of the cultured isolates obtained from soil by the procedure just described were tested by what shall be referred to herein as the "plant protection assay" for their ability to protect alfalfa seedlings from damping off caused by *Phytophthora meoasoerma* f. sp. *medicaginis* (hereinafter "Pmm"). The conventional alfalfa cultivar Iroquois, which is known to be vulnerable to Pmm, was used as the test plant. One gram of Iroquois alfalfa seeds was soaked in 18M sulfuric acid for 10 minutes. The seeds were then washed in 2 l. of sterile, distilled water and were placed in 10 ml. of sterile water and shaken at 28° C. for 24 hours. Next, the seed coats were removed manually with forceps, and the seedlings were planted in test tubes containing 5 ml. sterile, moist vermiculite. Three seedlings were planted in each test tube. Two days after the seedlings were planted, each test tube was inoculated with 0.3 ml. of a two-day-old culture of the bacterial isolate to be tested. In the case of ATCC 53522 and its mutants, that time is sufficient for the cultures to grow to saturation in TSB and sporulate. Then each tube immediately was inoculated with $10^3$ zoospores of Pmm.

After addition of the zoospores, the test tubes containing the plants were incubated at 24° C. with a 24 hour photoperiod for five days, at which time the plants were evaluated for symptoms of damping off. All control plants consistently were dead. Thus, the fact that a plant survived at all was evidence of at least minimal biological control exerted by the bacterial isolate being used. All bacteria that demonstrated that minimal amount of effectiveness for biological control of Pmm-caused damping off were retested by the same method to verify the consistency of the control. The screening procedure just described served as a plant protection assay, and all 500 isolates from the four sites in Wisconsin referred to above were tested by that assay.

Of the 500 isolates, only ATCC 53522 was identified as having the ability consistently to exert biological control of Pmm in Iroquois alfalfa, as evidenced by at least 20 separate experiments. ATCC 53522 appears to be *Bacillus cereus* (hereinafter *B.cereus*), based on physiological tests, its colony morphology, and its spore size, shape, and position. Thus, ATCC 53522 produces acetoin, forms an acid from glucose broth, hydrolizes starch, and grows in anaerobic agar. These characteristics, together with the colony morphology and the spore size, shape, and position observed in ATCC 53522, are cited as distinctively characteristic of *B.cereus* by R. E. Buchanan and N. E. Gibbons, co-editors (1974), *Bergey's Manual of Determinative Bacteriology,* 8th edition, pp. 532–535.

*B.cereus* is a not uncommon bacterium in field soils. However, strains of *B.cereus* demonstrating antifungal activity are almost unheard of. The inventors tested two known strains of conventional *B.cereus* obtained from entirely separate sources and found neither of them to exhibit the antifungal properties of ATCC 53522. Furthermore, of the 500 root-associated bacteria reviewed in the isolation process, many were probably *B.cereus* and, in fact, many of them had the same colony morphology as ATCC 53522. However, none of these other strains exhibited the antifungal qualities of ATCC 53522. *S. Wakavama et al.* (1984), *Antimicrob. Agents Chemother.,* 26, 939–940, describe antifungal activity in a strain of *B.cereus.* However, most of the antifungal antibiotics made by Bacillus are produced by strains of *Bacillus subtilis,* which is easily distinguishable from ATCC 53522. The antifungal toxin produced by ATCC 53522 differs from that of the strain of *B.cereus* described by *S. Wakayama et al.* in that the toxin of ATCC 53522 is of a lower molecular weight and has different solubility properties. In addition, ATCC 53522 differs from the reported *B.cereus* strain in that it grows anaerobically whereas the reported strain does not. Consequently, it is clear that the two *B.cereus* strains are not the same and that their toxins are not the same.

Both naturally occurring and artificially produced mutants of ATCC 53522 have been isolated. ATCC 53522 is generally sensitive to the antibiotic rifampicin and neomycin. However, naturally occurring mutants of ATCC 53522 have been prepared by plating ATCC 53522 on media containing each of those antibiotics. Resistant colonies were replated on the antibiotic-containing media. The mutants were then tested in the plant protection assay described above. Five mutants were isolated that were resistant to rifampicin, a sixth mutant was developed that was resistant to neomycin, and at least one additional mutant was isolated that was resistant to streptomycin. Each of these mutants protected alfalfa plants in the plant protection assay as effectively as did ATCC 53522.

Induced mutants of ATCC 53522 were prepared from a culture of vegetatively growing cells of ATCC 53522. The cells were diluted to a density of $10^8$ cells/ml, and a quantity of this culture was treated by exposure to one $\mu g/ml$ N-methyl-nitrosoguanidine for 30 minutes at room temperature. The cells then were washed with water, and dilution plates were prepared with TSA. The treatment with N-methyl-nitrosoguanidine was found to have killed 99% of the bacteria in the original culture. Thus, the remaining viable bacteria each had a high probability of containing at least one mutation. Of 500 such bacteria derived from independent colonies, 490 proved capable of protecting alfalfa plants against Pmm when tested by the plant protection assay.

It is clear from the information just disclosed that ATCC 53522 is well characterized and appears to be unique or at least uncommon. Furthermore, it is also clear that both naturally occurring and induced mutants of ATCC 53522 may be isolated by conventional methods well known to and within the scope of the skill of those skilled in this art.

It has now been discovered that ATCC 53522 and at least some of its mutants may be utilized in an effective method to enhance nodulation of legumes. The discovery of this method was entirely accidental and occurred as an ancillary observation of the effects of the bacterial strains referred to on the susceptibility of plants treated with those bacteria to damping off and root rot. The appearance has never been observed of ATCC 53522 or any of its mutants in nature in concentrations sufficient to produce the effect obtained by the method of the invention.

Stated in general terms, the method for enhancing nodulation in legumes includes placing an effective quantity of an enhancing bacteria selected from the group consisting of ATCC 53522, its enhancing mutants, and mixtures thereof in the immediate vicinity of the legume roots in which nodulation is to be enhanced. This placement can be conveniently accomplished by coating or co-planting the seed of the legume in which nodulation is to be enhanced with the bacteria. It is sometimes convenient that the enhancing bacteria be included in an enhancing inoculant. An enhancing inoculant consists essentially of an enhancing bacteria in a non-interfering carrier. Such a carrier shall be defined as one that does not prevent enhancement of legume nodulation by the enhancing bacteria. Preferably the carrier is a material that can be applied to seeds as a seed coating. The coating of legume seeds with Rhizobium bacteria is well known in the art, and the conventional materials and methods for so coating legume seeds are directly suitable for use with the enhancing bacteria disclosed herein.

Alternative methods of placing enhancing bacteria in the immediate vicinity of roots in which nodulation is to be enhanced will be apparent to one skilled in the art. Thus, it would be possible to spray seed, roots, or soil that is to be in immediate contact with seed or roots with a liquid culture medium or other carrier containing the enhancing bacteria. TSB is an example of a suitable liquid culture medium. Solid culture media such as TSA or another non-interfering solid carrier containing enhancing bacteria similarly could be mixed with soil to be placed in the immediate vicinity of legume seed or roots.

The following are particular examples of practice of the method of the invention.

EXAMPLE 1

Field testing of the method of enhancing root nodulation in soybeans using ATCC 53522

ATCC 53522 was cultured overnight in TSB. 1 ml. of the culture was then placed on a TSA plate, which then was incubated at 28° C. for 48 hours. The bacteria from the plate were suspended in from 1-2 ml of 1% methyl cellulose. This suspension was put into a 50 ml conical centrifuge tube with 20 soybean seeds. The soybean seeds were of the variety McCall and had been obtained from Olds Seed Co.: Madison, Wis. The centrifuge tube was vortexed vigorously until the soybeans were uniformly coated with the bacterial suspension. The seeds were then spread on dry Petri plates and allowed to dry in a laminar flow hood.

The coated seeds were planted at the University of Wisconsin Experimental Farm at Arlington, Wis., in a soil that was predominately Joy silt loam. Furrows were made in the soil with a wheel hoe. The seeds were placed in the furrows at a density of 8 seeds per linear foot, and the seeds were then covered to a depth of 1 inch. Methyl cellulose-coated seeds were used for controls.

The plants were grown to maturity, whereupon they were gently harvested, and the soil removed from their roots. Nodules were counted on 25 plants of each treatment. The results are as follows. The mean number of nodules is expressed ±the standard error:

| TREATMENT | NO. OF NODULES |
|---|---|
| Methyl Cellulose | 14.3 ± 1.2 |
| ATCC 53522 | 19.5 ± 1.0 |

The number of nodules for the control (methyl cellulose) treatment as opposed to the ATCC 53522 treatment differed significantly in a Least Significant Difference test at P=0.05. It was noted by non-quantitative observation that the roots of the plants that had been treated with ATCC 53522 were longer and generally more robust when compared to the roots of the control treatment, and the nodules that had formed on them were larger, firmer, and pinker than those characteristic of the control plants.

EXAMPLE 2

Field testing of the method of enhancing root nodulation in soybeans using mutants of ATCC 53522

Naturally occurring mutants of ATCC 53522 were obtained, one that was resistant neomycin (referred to herein as "mutant strain-Neo") and another resistant to streptomycin (herein after referred to "mutant strain-Str"). The mutant strains were obtained in the manner disclosed above in the specification with respect to other mutant strains isolated on the basis of their resistance to an antibiotic that normally kills or inhibits ATCC 53522. Both mutant strains were confirmed by the use of the plant assay method referred to above to provide protection from damping off.

The bacteria cultures were grown for seed coating by placing 1 ml of a TSB culture of the bacteria that had been growing overnight on a TSA plate. The plates were then incubated at 28° C. for 48 hours. The bacteria were scraped off the plates, 1–3ml of TSB was added, and they were placed into 50 ml conical centrifuge tubes along with 20 soybean seeds per tube. The seed used was soybean variety AgriPro 200 obtained from Agri Pro, Inc. Each tube was then vortexed vigorously until the bacteria and TSB were uniformly distributed over the seeds. The seeds then were spread on plates and allowed to dry in a laminar flow hood. The seeds were planted at the University of Wisconsin Experimental Farm at Arlington, Wis., in soil that was predominately Joy silt loam. Furrows were made with a wheel hoe. The seeds were placed in the furrows at a density of 2 seeds per linear foot and then were covered to a depth of 1 inch. Untreated seed was used as a control.

Each treatment consisted of two 30-foot rows replicated in three randomized blocks. At each sampling, three plants per treatment were chosen randomly and gently removed from each block for a total of nine plants per treatment per sampling. Roots were washed and nodules counted. Samplings occured at 21 days and 28 days after planting.

The results were as follows:

| TREATMENT | NO. OF NODULES PER PLANT | |
|---|---|---|
| | 21 days | 28 days |
| Control | 6.4 ± 1.47 | 9.0 ± 1.80 |
| Mutant-Neo | 9.0 ± 1.53 | 17.8 ± 2.00 |
| Mutant-Str | 8.8 ± 1.73 | 21.1 ± 2.20 |

Statistical analysis yielding the standard error shown as a±was performed by the Student's t-test. The difference between means was analyzed by Least Significant Difference. Both experimental treatments differed significantly from the controls. At the 21 day sampling, statistical analysis demonstrated a significant difference on the number of nodules at a P=0.1 confidence level. At the 28 day sampling, the significant difference was at the P=0.001 confidence level. The roots and nodules of the treated plants differed from those of the control plants in the same ways as those of Example 1.

Taken together, Examples 1 and 2 provide evidence of the ability of both ATCC 53522 and its enhancing mutants to significantly increase the numbers of nodules formed on the roots of legumes under actual field conditions. In addition to increased numbers of nodules, in each instance, plants that had been treated with an enhancing bacteria had larger nodules and longer roots. In general, the root systems appeared to be more "healthy" in appearance by non-quantitative estimation of skilled observers. Furthermore, nodule senescence or aging appeared to be reduced or delayed. Thus, while some of the nodules of the controlled plants had become soft and appeared to be in the process of losing structural integrity, the nodules of plants treated with an enhancing bacteria were firm and exhibited the pink color associated with active and functioning nodules.

It will be apparent to those skilled in the art that a number of modifications and changes can be made without departing from the spirit and scope of the present invention. Therefore, it is not intended that the invention be limited by the terms of the general disclosure above nor by the Examples but only by the claims, which follow.

What is claimed is:

1. A method for enhancing nodulation in legumes growing in a growing medium comprising the step of placing in the growing medium in the immediate vicinity of the roots of the legume the nodulation of which is to be enhanced an effective quantity of an enhancing bacteria selected from the group consisting of *Bacillus cereus* ATCC 53522, and enhancing mutants thereof.

2. The method of claim 1 wherein the step of placing an effective quantity of an enhancing bacteria in the immediate vicinity of the roots of the legume further comprises the step of applying the enhancing bacteria to seed prior to its being planted in the growing medium, whereupon the roots of the plant growing from the seed will have been placed in the immediate vicinity of the enhancing bacteria.

3. The method of claim 2 wherein the step of applying the enhancing bacteria to seed further comprises the steps of preparing an inoculant of the protecting bacteria consisting essentially of an enhancing bacteria and a non-interfering carrier, and coating the seed with the inoculant.

4. An inoculum for application to seeds for the enhancement of root nodulation in plants growing therefrom comprising
   (a) a non-interfering carrier and
   (b) an effective quantity of enhancing bacteria selected from the group of bacteria consisting of *Bacillus Cereus* ATCC 53522, and an enhancing mutant thereof.

* * * * *